(12) United States Patent
Saul et al.

(10) Patent No.: US 8,187,862 B2
(45) Date of Patent: May 29, 2012

(54) BIOREMEDIATION METHODS

(75) Inventors: Michael T. Saul, Cincinnati, OH (US);
Efrain Torres, Cincinnati, OH (US);
Peter A. Vandenbergh, Cincinnati, OH (US)

(73) Assignee: CL Solutions, Cincinnati, OH (US)

( * ) Notice: Subject to any disclaimer, the term of this patent is extended or adjusted under 35 U.S.C. 154(b) by 1032 days.

(21) Appl. No.: 11/682,519

(22) Filed: Mar. 6, 2007

(65) Prior Publication Data

US 2008/0220504 A1 Sep. 11, 2008

(51) Int. Cl.
*B09B 3/00* (2006.01)
*C02F 1/02* (2006.01)
*C02F 3/00* (2006.01)
*C02F 3/34* (2006.01)
*D06M 16/00* (2006.01)

(52) U.S. Cl. ........ 435/264; 210/600; 210/601; 435/262; 435/262.5; 435/876; 435/877

(58) Field of Classification Search ........................ None
See application file for complete search history.

(56) References Cited

U.S. PATENT DOCUMENTS

| 4,202,882 | A | * | 5/1980 | Schwartz ..................... 424/76.2 |
| 4,452,894 | A | | 6/1984 | Olsen et al. |
| 4,508,824 | A | | 4/1985 | Olsen |
| 4,593,003 | A | | 6/1986 | Vandenbergh |
| 4,800,158 | A | | 1/1989 | Vandenbergh |
| 4,853,334 | A | | 8/1989 | Vandenbergh et al. |
| 4,870,012 | A | | 9/1989 | Vandenbergh |
| 4,910,143 | A | | 3/1990 | Vandenbergh |
| 5,958,241 | A | * | 9/1999 | DeBenedetto et al. ....... 210/611 |
| 6,068,774 | A | * | 5/2000 | Vandenbergh et al. ....... 210/611 |
| 6,110,372 | A | | 8/2000 | Perriello |
| 6,245,552 | B1 | | 6/2001 | Glendening et al. |
| 6,762,047 | B2 | | 7/2004 | Vandenbergh |
| 6,884,301 | B2 | | 4/2005 | Haydu et al. |
| 7,056,061 | B2 | | 6/2006 | Kukor et al. |
| 2003/0235904 | A1 | * | 12/2003 | Vandenbergh ................ 435/264 |

OTHER PUBLICATIONS

John D. Brusenhan, P.E., et al., Aerobics to the Rescue, Pollution Engineering, Jan. 2006, 4 pages.

* cited by examiner

*Primary Examiner* — Debbie K Ware

(74) *Attorney, Agent, or Firm* — Thompson Hine LLP

(57) ABSTRACT

A method and composition for bioremediation of environmental material. In one embodiment, material to be bioremediated is debris is obtained from a metropolitan street cleaning operation. An environmentally safe all natural non-pathogenic microbial composition is used under conditions sufficient to bioremediate the material.

20 Claims, No Drawings

ID METHODS

FIELD OF THE INVENTION

Bioremediation of environmental material such as street sweeping debris.

DETAILED DESCRIPTION

A composition and method for bioremediation of environmental material containing at least one contaminant. In one embodiment, the environmental material is collected during a street sweeping process. The environmental material can be organic (e.g., mulch) and/or inorganic (e.g., sand). The contaminant can be organic (e.g., petroleum hydrocarbons) and/or inorganic (e.g., nitrates).

As used herein, bioremediation is one type of decontamination; other types of decontamination are chemical treatment, mechanical removal, and heat reduction. As used herein, a contaminant is any material that imparts an undesirable, but not necessarily toxic, property to the environmental material; the terms "contaminant' and "pollutant" are used synonymously. As used herein, the term "environmental material" refers to material to be bioremediated, and is used synonymously with the terms "matrix", "waste", "debris", and "spoils". Once a bioremediation composition is provided, the material is referred to herein as "treated material" or "bioremediated material", notwithstanding that complete bioremediation may require subsequent treatment, subsequent treatment time, etc. Any level of contaminant reduction from untreated material is encompassed by the disclosed bioremediation method; bioremediation to an extent that no contaminant(s) are detected (e.g., 100% bioremediation) may but need not occur.

In one embodiment, the bioremediation composition is, or contains, one strain of one species of non-pathogenic *Psuedomonas* microorganisms. In another embodiment, the bioremediation composition is, or contains, at least two strains of one species of non-pathogenic *Psuedomonas* microorganisms. In another embodiment, the bioremediation composition is, or contains, one strain of each of at least two species of non-pathogenic *Psuedomonas* microorganisms. In embodiments containing more than one strain, the *Pseudomonas* species may be the same or different. In embodiments containing more than one strain and/or more than one species, the composition blend may contain different ratios of strains and/or species. The composition is also referred to herein as a microbial consortium. The composition is used at a sufficient *Pseudomonas* concentration and sufficient oxygen to support microbial growth.

In all embodiments, the composition is capable of degrading hydrocarbon and/or other organic contaminants and/or inorganic contaminants under appropriate environmental conditions, thus resulting in bioremediation, as subsequently described. In one embodiment, hydrocarbons, organic solvents, and semi-volatile hydrocarbons are converted into harmless, naturally recyclable by-products. In one embodiment, the composition and method are used to bioremediate street cleaning debris, e.g., from a city street cleaning program.

As used herein, bioremediation includes any qualitative and/or quantitative reduction in at least one contaminant, either organic or hydrocarbon contaminant, and may include bioaugmentation of a contaminated matrix's inherent or acquired microbial population (e.g., organic waste such as soil, etc.). In one embodiment, bioremediation includes reduction of at least one contaminant such that the contaminant is no longer detectable in the contaminated material or is reduced to an acceptable amount or concentration in the material.

Any environmental material containing or thought to contain contaminated material or materials may be bioremediated according to the method. As non-limiting examples used for illustration only, contaminated materials include, but are not limited to, plant matter, gravel, pebbles, stone, stone chips, rock, asphalt, concrete, brick, wood, glass, soil, mulch, metals, plastics, paper, and paper materials.

One embodiment of the method results in bioremediation of at least one inorganic nitrate contaminant. An inorganic nitrate contaminant includes, but is not limited to, Group Ia and Group IIa metal nitrates (e.g., lithium nitrate, sodium nitrate, potassium nitrate, magnesium nitrate, and calcium nitrate). In one embodiment, the inorganic nitrate contaminant may be a fertilizer such as ammonium nitrate fertilizers.

Another embodiment of the method results in bioremediation of at least one contaminant contained in crude and/or refined petroleum. These petroleum contaminants include combinations of aliphatic hydrocarbons (e.g., straight or branched chain hydrocarbons having a chain length ranging from about $C_5$-$C_{36}$) and aromatic hydrocarbons (e.g., at least one ring structure ranging from $C_9$-$C_{22}$ hydrocarbons). Examples of such contaminants include, but are not limited to, tars, creosote, crude oil, refined oil, fuel oils (e.g., Nos. 2, 4, and 6 fuel oils), diesel oils, gasoline, hydraulic oils, kerosene, chrysene, cresol, cyclohexanone, ethylbenzene, butylbenzene, ethyl acetate, fluorine, isoprenoids, methyl ethylacetate, 2-butanone, methyl pentanone, methyl propylacetate, butylacetate, petroleum oils and greases, phenanthrene, phenol, Stoddard solvents, mineral spirits, terpene-based compounds, phthalates such as bis(2)ethylhexylphthalate and/or dioctylphthalate, and/or phenolic compounds.

As one example, the most volatile components of gasoline are benzene, toluene, ethylbenzene, and xylenes. These volatile components may be present as petroleum constituents in gasoline-contaminated media and may be bioremediated according to the method. As another example, with respect to fuel oils and heavier petroleum products, constituents that may be present as contaminants include, but are not limited to, trimethylbenzenes, other polycyclic aromatic hydrocarbons (PAH) such as naphthalene, anthracene, acenaphthene, acenaphthylene, benzo(a)anthracene, benzo(a)pyrene, benzo (b) fluoranthene, benzo(g,h,i)perylene, benzo(k)fluoranthene, and pyrene, and may be bioremediated according to the method.

Petroleum contaminants in a material may be accompanied by other pollutants such as halogenated aliphatic and aromatic compounds (e.g., chlorinated aliphatic and chlorinated aromatic compounds). Specific chlorinated hydrocarbon contaminants include, but are not limited to, aldrin, trichloroethylene, tetrachloroethylene, 1,2-dichloroethane, carbon tetrachloride, chlorobenzene, chlorotoluenes, dichlorobenzene, dichloroethanes, dichloroethylene, dichlorotoluene, tetrachloroethane, trichloroethane, pentachlorophenol, vinyl chloride, etc.

The method may be used in any of the following embodiments, each of which typically contains at least one contaminant. In one embodiment, the contaminated material is a mixture of contaminants collected from a street cleaning operation. It is referred to herein as street sweeping debris, and is contaminated material generated during routine cleaning and/or sweeping of road surfaces. It typically contains soil, rock, asphalt, sand, leaves, and other vegetative matter. Street sweeping debris may also contain amounts of other solid wastes that are often discarded along streets, roads, etc.

For example, street sweeping debris may contain from about 5% to about 40% trash, which may include paper, glass, and/or plastics. In another embodiment, the contaminated material may be street sweeping debris collected at a site of a chemical spill (e.g. a petroleum oil spill). In another embodiment, the contaminated material may be debris generated during maintenance of a city infrastructure (road repair, construction, utility maintenance, etc.). In another embodiment, the contaminated material may be explosive-associated debris (e.g., weapons training site, weapons manufacture, weapons testing, war zones, cleanup from a terrorist attack excluding radioactive material). In another embodiment, the contaminated material may be debris at a fuel terminal (e.g., air, naval, rail, automobile, etc.), such as a gasoline station. In another embodiment, the contaminated material is debris associated with transportation industries such as railroads, airports, shipping terminals, parking areas, loading and/or unloading areas, etc. In another embodiment, the contaminated material is associated with the manufacture of certain gases. In another embodiment, the contaminated material is produced at wood treatment facilities. In another embodiment, the contaminated material may be produced at an industrial manufacturing site. In another embodiment, the contaminated material may be catch basin sediments comprising primarily soil, rocks, asphalt, vegetative matter, and solid waste collected in settling structures designed to receive stormwater runoff from roads and/or from industrial manufacturing sites. In another embodiment, the contaminated material may be collected from a roadside ditch. Other contaminants and industries in which the method may be used are known to one skilled in the art, non-limiting examples include treatment of waste water, cutting fluids, coolants, etc.

The street sweeping debris treated by the disclosed method may include any contaminated materials normally found in municipal street sweeping waste. For example, street sweeping waste may include soil, rocks, gravel, asphalt, leaves and other vegetative matter such as landscape clippings, dirt, litter, metals, glasses, and/or sand in any combination. Other components of street sweeping waste are known to one skilled in the art. Additionally, one skilled in the art would recognize that the composition of street sweeping debris depends on several factors including, but not limited to, the geographical location of the street sweeping operation and ambient weather conditions and patterns. As one example, street debris collected in coastal or desert areas could have a relatively larger portion of sand than street debris in other geographic areas. As another example, street debris collected in an area with heavy forestation could have a relatively larger portion of decaying organic vegetation than street debris in other geographic areas.

The method provides at least one non-pathogenic microorganism of the genus *Pseudomonas* capable of degrading at least one contaminant. *Pseudomonas* is a naturally occurring Gram negative, aerobic, rod-shaped bacteria.

In one embodiment, a composition is added to the debris. In one embodiment, the composition contains at least one of *Psuedomonas putida* strain B and *Psuedomonas putida* strain E. In one embodiment, the composition is a 50:50 combination of strains B and E, commercially available as PETROX® 1 (Osprey Biotechnics, Sarasota Fla.). In one embodiment, the composition is at least one of *Pseudomonas fluorencens* strain F and *Psuedomonas putida* strain I. In one embodiment, the composition is a 50:50 combination of strains F and I, commercially available as Petrox® 3 (Osprey). In one embodiment, the only bacteria in the composition is *Pseudomonas putida* strain B. In one embodiment, the only bacteria in the composition is *Pseudomonas putida* strain E.

In one embodiment, the only bacteria in the composition is *Pseudomonas fluorencens* strain F. In one embodiment, the only bacteria in the composition is *Pseudomonas putida* strain I. *Psuedomonas putida* strain B was deposited under accession number NRRL B-18117 on Oct. 8, 1986 at Agricultural Research Service Culture Collection (NRRL), Agricultural Research Service, USDA, 1815 North University Street, Peoria Ill. 61604-3999. *Psuedomonas putida* strain E was deposited under accession number NRRL B-18118 on Oct. 8, 1986 at Agricultural Research Service Culture Collection (NRRL), Agricultural Research Service, USDA, 1815 North University Street, Peoria Ill. 61604-3999. *Psuedomonas florencens* strain F was deposited under accession number NRRL B-21658 on Jan. 21, 1997 at Agricultural Research Service Culture Collection (NRRL), Agricultural Research Service, USDA, 1815 North University Street, Peoria Ill. 61604-3999. *Psuedomonas florencens* strain G was deposited under accession number NRRL B-18296 on Jan. 21, 1988 at Agricultural Research Service Culture Collection (NRRL), Agricultural Research Service, USDA, 1815 North University Street, Peoria Ill. 61604-3999. *Psuedomonas putida* strain I was deposited under accession number NRRL B-30044 on Aug. 6, 1998 at Agricultural Research Service Culture Collection (NRRL), Agricultural Research Service, USDA, 1815 North University Street, Peoria Ill. 61604-3999

In one embodiment, a suitable *Pseudomonas* strain is naturally occurring within the debris. In this embodiment, the indigenous microbial population may be stimulated by introducing nutrients and/or growth factors to the debris, and/or the indigenous microbial population may be supplemented by introducing one or more of the previously described compositions. Nutrients and growth factors include, e.g., dextrose, sucrose, nitrate (potassium, sodium nitrate), soy extract, yeast extract, etc. Other methods for stimulating the indigenous microbial population of a contaminated material are known to one skilled in the art and may be used in combination with the disclosed methods.

*Pseudomonas* is capable of degrading a wide range of organic compounds and certain inorganic compounds, including petroleum hydrocarbons, organic solvents, inorganic nitrate compounds, and semi-volatile hydrocarbons, into harmless by-products such as carbon dioxide and water by the complete metabolism of the petroleum hydrocarbon. The ability of *Pseudomonas* to degrade organic chemicals has been known at least since the 1960s.

In one embodiment, the composition is or contains a lyophilized non-pathogenic *Pseudomonas* strain. In one embodiment, the composition is or contains *Pseudomonas putida* strain B deposited with the Northern Regional Research Laboratory (NRRL) (Microbial Genomics and Bioprocessing Research Unit, National Center for Agricultural Utilization Research, Peoria Ill.) under accession number NRRL-B-18117. In another embodiment, the composition is or contains *Pseudomonas putida* strain E (NRRL-B-18118). In another embodiment, the composition is or contains *Pseudomonas fluorescens* strain F (NRRL-B-21658). In another embodiment, the composition is or contains *Pseudomonas putida* strain I (NRRL-B-30044).

Single strains and compositions containing mixtures (also referred to as consortium) of strains (e.g., 50:50 mixtures) are available at least from Osprey Biotechnics (Sarasota Fla.), Northern Regional Research Laboratory (NRRL) (Microbial Genomics and Bioprocessing Research Unit at the National Center for Agricultural Utilization Research, Peoria Ill., etc. As one example, in one embodiment, the composition is or contains PETROX® 1 (CI Soutions, Cold Springs Ky.), a 50:50 mixture of *Pseudomonas putida* strains B and E, and capable of biodegrading benzene, toluene, ethylbenzene, xylene, 2,5-dichlorotoluene, dioctylphthalate, ethyl benzene, gasoline fuel, diesel fuel, heating oils, unrefined oil, methyl ethyl ketone, methylene chloride, mineral spirits, naphthalene, Stoddard solvents, toluene, and/or xylenes. In one embodiment, the ratio by weight of *Pseudomonas putida* strain B to *Pseudomonas putida* strain E ranges from about 99:1 to about 80:20, or from about 1:99 to about 20:80. In another embodiment, the ratio by weight of *Pseudomonas putida* strain B to *Pseudomonas putida* strain E ranges from about 80:20 to about 60:40, or from about 20:80 to about 40:60. In another embodiment, the ratio by weight of *Pseudomonas putida* strain B to *Pseudomonas putida* strain E ranges from about 60:40 to about 50:50, or from about 40:60 to about 50:50. In still another embodiment, the ratio by weight of *Pseudomonas putida* strain B to *Pseudomonas putida* strain E is about 50:50.

As another example, in one embodiment, the composition is or contains PETROX® 3 (CI Solutions, Cold Springs Ky.), a 50:50 mixture of *Pseudomonas fluorescens* strain F and *Pseudomonas putida* strain I, and capable of biodegrading anthracene, chlorotoluenes, chrysene, cresols, creosote, fluorine, food and petroleum oils and greases, dichlorophenoxyacetic acids, aldrin, endrin, pentachlorophenol, phenanthrene, and/or phenol. In one embodiment, the ratio by weight of *Pseudomonas fluorescens* strain F to *Pseudomonas putida* strain I ranges from about 99:1 to about 80:20, or from about 1:99 to about 20:80. In another embodiment, the ratio by weight of *Pseudomonas fluorescens* strain F to *Pseudomonas putida* strain I ranges from about 80:20 to about 60:40, or from about 20:80 to about 40:60. In another embodiment, the ratio by weight of *Pseudomonas fluorescens* strain F to *Pseudomonas putida* strain I ranges from about 60:40 to about 50:50, or from about 40:60 to about 50:50. In another embodiment, the ratio by weight of *Pseudomonas fluorescens* strain F to *Pseudomonas putida* strain I is about 50:50.

In one embodiment, the composition is or contains a mixture of PETROX® 1 and PETROX® 3. In one embodiment, the ratio by weight of PETROX® 1:PETROX® 3 ranges from about 99:1 to about 80:20, or from about 1:99 to about 20:80. In another embodiment, the ratio by weight of PETROX® 1:PETROX® 3 ranges from about 80:20 to about 60:40, or from about 20:80 to about 40:60. In another embodiment, the ratio by weight of PETROX® 1:PETROX® 3 ranges from about 60:40 to about 50:50, or from about 40:60 to about 50:50. In another embodiment, the ratio by weight of PETROX® 1:PETROX® 3 ranges from about 95:5 to about 5:95. In another embodiment, the ratio by weight of PETROX® 1:PETROX® 3 ranges from about 80:20 to about 60:40, or from about 20:80 to about 40:60.

In one embodiment, the composition is or contains CL-OUT™, which is a mixture of *Pseudomonas putida* stains B and E and *Pseudomonas fluorescens* strain G (NRRL-B-18296) with nutrients and growth factors, available from Cl-solutions (Cold Spring Ky.). The three *Pseudomonas* strains in CL-OUT™ are in a ratio of about 1:1:1. One skilled in the art will appreciate that the ratio may be varied to optimize biodegradation. CL-OUT™ is capable of effectively biodegrading chlorinated contaminants including, but not limited to, carbon tetrachloride, chlordane, chlorobenzene, dichlorobenzene, dichloroethanes, dichloroethylene, dichloropropane, dinoctylphthalate, methylene chloride, MTBE, tetrachloroethane, tetrachloroethylene, trichloroethane, trichloroethylene, and vinyl chloride.

In one embodiment, the composition is or contains any suitable mixture of CL-OUT™ and PETROX® 1. In one embodiment, the ratio by weight of PETROX® 1:CL-OUT™ may be from about 99:1 to about 80:20, or from about 1:99 to about 20:80. In one embodiment, the ratio by weight of PETROX® 1:CL-OUT™ may be from about 80:20 to about 60:40, or from about 20:80 to about 40:60. In one embodiment, the ratio by weight of PETROX® 1:CL-OUT™ may be from about 60:40 to about 50:50, or from about 40:60 to about 50:50. In one embodiment, the ratio by weight of PETROX® 1:CL-OUT™ may be from about 95:5 to about 5:95. In one embodiment, the ratio by weight of PETROX® 1:CL-OUT™ may be about 50:50.

In one embodiment, the composition is or contains any suitable mixture of CL-OUT™ and PETROX® 3. In one embodiment, the ratio by weight of PETROX 3™:CL-OUT™ may be from about 99:1 to about 80:20, or from about 1:99 to about 20:80. In one embodiment, the ratio by weight of PETROX® 3:CL-OUT™ may be from about 80:20 to about 60:40, or from about 20:80 to about 40:60. In one embodiment, the ratio by weight of PETROX® 3:CL-OUT™ may be from about 60:40 to about 50:50, or from about 40:60 to about 50:50. In one embodiment, the ratio by weight of PETROX® 3:CL-OUT™ may be from about 95:5 to about 5:95. In one embodiment, the ratio by weight of PETROX® 3:CL-OUT™ may be about 50:50.

In one embodiment, the composition is or contains any suitable mixture of CL-OUT™, PETROX® 1, and PETROX® 3. In one embodiment, the ratio of CL-OUT™:PETROX® 1:PETROX® 3 may be about 33:33:33. In one embodiment, the ratio of CL-OUT™:PETROX® 1:PETROX® 3 may be about 50:25:25, or 25:50:25, or 25:25:50. In one embodiment, the ratio of CL-OUT™:PETROX®1:PETROX®3 may be about 10:10:80, or 10:80:10, or 80:10:10. In one embodiment, the ratio of CL-OUT™:PETROX® 1:PETROX® 3 may be about 5:90:5, or 5:5:90, or 90:5:5. In one embodiment, the ratio of CL-OUT™:PETROX® 1:PETROX® 3™ may be about 20:40:40, or 40:20:40, or 40:40:20.

In each of the preceding sections, the ratios are not limiting and serve to illustrate the scope of the method. One skilled in the art will be able to provide other ratios to achieve bioremediation without undue experimentation.

In one embodiment, the composition of PETROX® and/or CL-OUT™, and any suitable combinations thereof may be applied as a stand-alone composition. In another embodiment, the composition of PETROX® and/or CL-OUT™, and any suitable combinations thereof may be used in combination with any other suitable decontamination solution. Examples of suitable decontamination solutions include vapor stripping, sparging, low temperature thermal treatment, chemical destruction, and dual-phase extraction solutions. Additional remediation methods are known to one skilled in the art and may be used in combination with the disclosed methods.

In one embodiment, the bioremediation method may use *Pseudomonas putida* NRRL-B-18117, *Pseudomonas putida* NRRL-B-18118, and/or *Pseudomonas fluorescens* NRRL-B-18296.

In one embodiment, the microbial consortium is or may contain from about 5% to about 95% *Pseudomonas putida* NRRL-B-18117 and from about 95% to about 5% *Pseudomonas putida* NRRL-B-18118. In another embodiment, the microbial consortium is or may contain about 25% to about 75% *Pseudomonas putida* NRRL-B-18117 and from about 75% to about 25% *Pseudomonas putida* NRRL-B-18118. In another embodiment, the microbial consortium is or may contain about 40% to about 60% *Pseudomonas putida* NRRL-B-18117 and from about 60% to about 40% *Pseudomonas putida* NRRL-B-18118. In another embodiment, the microbial consortium is or may contain about 50% *Pseudomonas putida* NRRL-B-18117 and about 50% *Pseudomonas putida* NRRL-B-18118.

In one embodiment, the microbial consortium is or may contain from about 5% to about 95% *Pseudomonas putida* NRRL-B-18117 and from about 95% to about 5% *Pseudomonas fluorescens* NRRL-B-18296. In another embodiment, the microbial consortium is or may contain about 25% to about 75% *Pseudomonas putida* NRRL-B-18117 and from about 75% to about 25% *Pseudomonas fluorescens* NRRL-B-18296. In another embodiment, the microbial consortium is or may contain about 40% to about 60% *Pseudomonas putida* NRRL-B-18117 and from about 60% to about 40% *Pseudomonas fluorescens* NRRL-B-18296. In another embodiment, the microbial consortium is or may contain about 50% *Pseudomonas putida* NRRL-B-18117 and about 50% *Pseudomonas fluorescens* NRRL-B-18296.

In one embodiment, the microbial consortium is or may contain from about 5% to about 95% *Pseudomonas putida* NRRL-B-18118 and from about 95% to about 5% *Pseudomonas fluorescens* NRRL-B-18296. In another embodiment, the microbial consortium is or may contain about 25% to about 75% *Pseudomonas putida* NRRL-B-18118 and from about 75% to about 25% *Pseudomonas fluorescens* NRRL-B-18296. In another embodiment, the microbial consortium is or may contain about 40% to about 60% *Pseudomonas putida* NRRL-B-18118 and from about 60% to about 40% *Pseudomonas fluorescens* NRRL-B-18296. In another embodiment, the microbial consortium is or may contain about 50% *Pseudomonas putida* NRRL-B-18118 and about 50% *Pseudomonas fluorescens* NRRL-B-18296.

The methods may be accomplished at any suitable *Pseudomonas* population and/or concentration effective to bioremediate the desired waste and/or contaminant(s). In one embodiment, the microbial consortium population may be from about 1% to about 100% of the total microbial population in the waste or contaminants. In another embodiment, the microbial consortium population may be from about 5% to about 95% of the total microbial population in the waste or contaminants. In another embodiment, the microbial consortium population may be from about 20% to about 80% of the total microbial population in the waste or contaminants.

In one embodiment, the composition is freeze dried. A quantity of the composition is portioned into a drum liner package, similar to liner bag used in garbage cans. In use, the package containing the composition is opened and fit into a drum, then water is added to each liner in its drum to rehydrate and activate the microorganisms.

The method may use any moisture level sufficient to maintain an effective *Psuedomonas* population in the material to be bioremediated. In one embodiment, the moisture level within the contaminated material is maintained from about 5% by weight to about 35% by weight of waste or contaminants. In one embodiment, the moisture level within the contaminated material is maintained from about 10% by weight to about 30% by weight of waste or contaminants. In one embodiment, the moisture level within the contaminated material is maintained from about 15% by weight to about 25% by weight of waste or contaminants. The moisture levels may be maintained by adding water in any suitable manner (e.g., sprinkling intermittently or at desired intervals, humidifying, etc.). Maintaining such a moisture level aids in maintaining a temperature range in the treated material conducive to microbial bioremediation.

The method may use any oxygen concentration within the contaminated material sufficient to maintain an effective *Psuedomonas* population in the material to be bioremediated. In one embodiment, oxygen may be dissolved in water contained within voids of the waste or contaminant(s) in a concentration from about 1 mg oxygen per 1 L water, to about 15 mg oxygen per 1 L water. In one embodiment, oxygen may be dissolved in water contained within voids of the waste or contaminant(s) in a concentration from about 3 mg oxygen per 1 L water, to about 12 mg oxygen per 1 L water. In one embodiment, oxygen may be dissolved in water contained within voids of the waste or contaminant(s) in a concentration from about 5 mg oxygen per 1 L water, to about 10 mg oxygen per 1 L water. In one embodiment, oxygen may be present in the vapors within the pores of the waste or contaminant(s) from about 15% by volume to about 25% by volume. In one embodiment, oxygen may be present in the vapors within the pores of the waste or contaminant(s) from about 17% by volume to about 24% by volume. In one embodiment, oxygen may be present in the vapors within the pores of the waste or contaminant(s) from about 19% by volume to about 21% by volume. In one embodiment, oxygen may be present in the vapors within the pores of the waste or contaminant(s) at about 21% by volume. Oxygen may be maintained in the water or vapor by methods known to one skilled in the art, e.g., by blowing air into the waste or contaminant(s), adding oxygen-releasing or oxygen-generating chemicals, adding compressed oxygen gas, etc.

The method may use any temperature sufficient to maintain an effective *Psuedomonas* population in the material to be bioremediated. In one embodiment, the material may be maintained at a temperature ranging from about 40° F. to about 105° F. In another embodiment, the material may be maintained at a temperature ranging from about 50° F. to about 95° F. In another embodiment, the material may be maintained at a temperature from about 70° F. to about 90° F. The temperature may be maintained and monitored using methods known to one skilled in the art, e.g., using external heaters to increase the internal temperature of the material to a desired temperature, covering the material to conserve internal heat, adding excess water to cool the material via evaporation, etc.

The method may use any pH sufficient to maintain an effective *Psuedomonas* population in the material to be bioremediated. In one embodiment, the pH within the material ranges from about pH 4 to about pH 9. In another embodiment, the pH within the material ranges from about pH 5 to about pH 8. In another embodiment, the pH within the material ranges from about pH 6 to about pH 8. In another embodiment, the pH within the material to be bioremediated is about pH 7. The pH many be maintained by the addition of caustic or acidic compounds to the material, and monitored using methods known to one skilled in the art.

In one embodiment, the microbial composition(s) may be activated by the addition of any suitable nitrate source. In one embodiment, the nitrate source may be present in an amount of from about 0.2 mg of the nitrate source per gram of the material to be bioremediated, to about 2 mg of the nitrate source per gram of the material to be bioremediated. In one embodiment, the nitrate source may be present in an amount of from about 0.35 mg of the nitrate source per gram of the material to be bioremediated, to about 1.5 mg of the nitrate source per gram of the material to be bioremediated. In one embodiment, the nitrate source may be present in an amount of from about 0.5 mg of the nitrate source per gram of the material to be bioremediated, to about 1 mg of the nitrate source per gram of the material to be bioremediated. In one embodiment, the nitrate source is monoammonium phosphate. In another embodiment, the nitrate source is ammonium nitrate or an alkali metal nitrate. Additional nitrate sources are known to one skilled in the art and may be used as a microbial activator.

The method may be accomplished over any time sufficient to maintain an effective *Psuedomonas* population to bioremediate the sample. In one embodiment, the time ranges from about 3 days to about 90 days. In one embodiment, the time ranges from about 30 days to about 180 days. In another example, the time ranges from about 90 days to about 300 days. In another embodiment, the time is about 21 days. Because bioremediation time depends on several factors including, but not limited to, contaminant concentration, microbial population, moisture content within the contaminated sample, oxygen content within the contaminated sample, weather conditions such as temperature, wind speed, and humidity, one skilled in the art would appreciate that treatment times may vary.

The method may be accomplished with the material in any configuration effective to permit bioremediation. In one embodiment, the material is configured into a windrow of any suitable dimensions. Dimensions are determined by factors such as material porosity, moisture content, and texture, expected ambient conditions such as temperature, humidity, and wind velocity, etc. As a non-limiting example of one embodiment, the windrow may have a length from about 5 m to about 100 m, a width from about 1 m to about 3 m, and a height of about 0.25 m to about 3 m. The windrow may have any geometric shape. The windrow height may be minimized to reduce overheating of the material to be bioremediated. For example, because the organic matter of plant vegetation provides nutrients for microbes, a windrow having a relatively high abundance of vegetation may exhibit enhanced microbial activity thereby increasing its internal temperature. Thus, the temperature of such a windrow may be controlled by limiting the dimensions of the windrow and providing an appropriate amount of moisture. Only a relatively small amount of nutrients, if any, may be necessary to add to such a windrow. In contrast, a windrow comprising a relatively large portion of sand and a relatively small portion of vegetation may exhibit decreased microbial activity, thereby decreasing its internal temperature. The dimensions of such a windrow may be increased, and it may be necessary to add a relatively large amount of nutrients.

In one embodiment, existing street sweeping equipment, generally known to one skilled in the art, is configured to contain and/or provide the composition to the material. Such equipment generally is a vehicle containing or adaptable to contain an inflow conduit used to collect the material (e.g., a vacuum hose), a hopper in which to contain the collected material during transit, and optionally a device to shred the material. Examples of street sweeping equipment include, but are not limited to, mechanical broom sweepers, vacuum sweepers, and regenerative air sweepers. In one embodiment, the equipment has an optional nozzle for providing liquid such as water. In one embodiment, the composition (the microbial consortium) contacts the contaminated material at the time the material is collected from the street. In another embodiment, the composition contacts the material before it is collected from the street, either immediately before or at a suitable time period before collection. In another embodiment, the composition contacts the material after it is collected from the street, either immediately after or at a suitable time period after collection. In the embodiment where the street sweeping equipment contains a nozzle, the material may be treated with water and/or the composition at any time, depending whether the nozzle is directed toward the inflow conduit or the hopper of the vehicle.

In another embodiment, a high-efficiency dry vacuum sweeper is fitted with at least one spray nozzle for spraying the street sweeping material in the hopper, immediately upon collection or thereafter, with the composition.

In any of the above embodiments, the bioremediated material is more efficiently disposed of than non-bioremediated material (i.e., contaminated or potentially contaminated street sweeping debris). As one example, bioremediated material may be safely removed off site, e.g., to a landfill, without the need for transport of toxic or potentially toxic material. As another example, material may be removed and bioremediated during transport so that the material arriving at a landfill or other site is at least partially bioremediated.

In one embodiment, the method augments the natural or acquired microbial population of material to be bioremediated.

The composition and method will be further appreciated with respect to the following non-limiting examples.

Example 1

The city of Portland Oreg., collected about 30,000 tons of debris from its seasonal street sweeping operations. The city paid about $28 per ton to landfill the collected debris, resulting in a cost exceeding $1,000,000. Use of the method was evaluated to reduce or eliminate tipping fees for disposal, which may be considerably more expensive if the material contains contaminants and/or cannot be used as landfill cover, to decrease the need to purchase virgin aggregates, and to offset operating costs through sales of bioremediated street sweeping debris as mulch.

Glass, metal, and large pieces of debris were removed by mechanical screens. The material, containing petroleum-based contaminants, was moved to a test area and formed into a windrow that was about two feet high, about 100 feet long, and about 8 feet wide. A SCAT windrow turner aerated and homogenized the material by carrying it several feet above its initial level and dropping it back to the ground.

A lyophilized bioremediation composition, resulting in a viable freeze dried form, was delivered to the site in a drum liner package. Four drums, each containing lyophilized PETROX 18, were maintained at ambient outdoor temperature for about 24 hr. Each of the four drams was transferred into a tank and 280 gallons of water was added to form a solution (500 gallons).

Existing equipment used in compositing operations was used to provide an even spray to the aerated material as it fell back to the ground to mix with the composition. For example, turning equipment was used to lift the material off the ground and turn it. The composition was provided in a substantially uniform spray using conventional spraying equipment (e.g., a hydroseeder) such that the composition uniformly contacted the material as aerated material fell to the ground. One treatment was used. In embodiments, more than one treatment may be used.

Samples of the treated material were collected prior to treatment (control samples) and at intervals of three, seven, and twenty-one days after treatment. Temperature of the material was monitored daily for the duration of treatment. If the temperature approached 95° F., water was applied to the material under conditions to maintain the temperature below about 95° F. A hose was used as a water sprinkler system to maintain moisture levels in the treated material (material after application of the composition). Other sprinkler systems (e.g., a in-ground sprinkler system) may be used.

The *Psuedomonas* population in the control sample and the treated material was quantitated by a standard plate count procedure according to methods known to one skilled in the art. Briefly, 1.00 g dry *Psuedomonas* sample or 1.0 ml liquid *Psuedomonas* sample was added to a 99 ml dilution blank, providing a $1 \times 10^2$ dilution. Dilutions were continued to yield about 30 cfu/ml to about 300 cfu/ml (i.e., 0.1 ml of a $1 \times 10^6$ dilution) when 0.1 ml aliquot was plated on trypticase soy agar (BBL, prepared according to manufacture's instructions) in plastic 100 mm×15 mm Petri plates) and incubated at 25° C. for 48 hours. Plates were counted and number of colonies and/or specific dilutions were recorded. Plating of dilutions of interest was performed at least in duplicate. Results were reported as the average of all counts (between 30 colonies and 300 colonies) for a specific dilution times the reciprocal of that dilution. Numbers were reported as cfu/g or cfu/ml depending upon whether the material was a solid or liquid.

Upon complete application of the composition the parameters were as follows. The population of *Pseudomonas* in the treated material ranged from about $1\times10^6$ cfu/ml to about $2.5\times10^6$ cfu/ml. This was about 10% of the natural aerobic microbial population (from about $1.5\times10^7$ cfu/ml to about $2.6\times10^7$ cfu/ml). The moisture level in the treated material was about 30% as measured by a field moisture testing instrument. Throughout the three-week bioremediation treatment, the moisture level within the treated material was maintained at about 30% by periodic sprayings with appropriate volumes of water using standard spraying techniques (e.g. sprinklers).

The treated sample was bioremediated by the method, demonstrated from reduction in the levels of benzo(a)pyrene and benzo(b)fluoranthene contaminants. For example, after seven days of treatment with the composition, the concentration of benzo(a)pyrene decreased from 140 μg/kg to 0 μg/kg, where μg/kg is μg of petroleum pollutant per kg treated sample. This was a 100% reduction of benzo(a)pyrene in the material. After seven days of treatment with the composition, the concentration of benzo(b)fluoranthene decreased from 210 μg/kg to 0 μg/kg, a 100% reduction of benzo(b)fluoranthene in the material. The method also reduced other PAH within the treated material. For example, after seven days of treatment with the composition, the concentration of chrysene decreased from 231 μg/kg to 171 μg/kg (26% reduction), the concentration of fluoranthene decreased from 264 μg/kg to 201 μg/kg (24% reduction), and the concentration of pyrene decreased from 344 μg/kg to 224 μg/kg (35% reduction). Results are shown in Table I.

TABLE I

RESULTS USING 7 DAYS PETROX ® 1 TREATMENT

| Petroleum Contaminant | Initial concentration (μg/kg) | Concentration after 3 days of PETROX ® 1 treatment | Concentration after 7 days of PETROX ® 1 treatment | Change (%) |
|---|---|---|---|---|
| Benzo(a)anthracene | ND | ND | ND | NA |
| Benzo(a)pyrene | 140 | 73.2 | ND | 100 |
| Benzo(b)fluoranthene | 210 | 139 | ND | 100 |
| Benzo(g,h,i)perylene | ND | 66.8 | ND | NA |
| Benzo(k)fluoranthene | ND | 70.6 | ND | NA |
| Chrysene | 231 | 152 | 171 | 26 |
| Fluoranthene | 264 | 149 | 201 | 24 |
| Pyrene | 344 | 225 | 224 | 35 |

μg/kg = μg contaminant per kg material;
ND = not detected

Results after treating an identical sample with a PETROX® 1 composition for 21 days are shown in Table II. With respect to benzo(a)pyrene, the PETROX®-7 day treated sample had a faster rate of degradation than the control sample. For example, while the PETROX®-7 day treated sample showed complete (100%) degradation of benzo(a) pyrene within the three week period, the PETROX® 1-21 day treated sample reduced the concentration of benzo(a)pyrene in the treated sample from 110 μg/kg to 95.9 μg/kg (13% reduction). While not being bound by any theory, the measurable degradation of petroleum contaminants in the untreated control samples may be attributable to naturally occurring bacteria within the sample.

TABLE II

RESULTS USING 21 DAYS PETROX ® 1 TREATMENT

| Contaminant Polycyclic Aromatic Hydrocarbons (PAH) (μg/kg) | Initial Sample | | Final Sample | | Change (%) | |
|---|---|---|---|---|---|---|
| | PETROX ® 1 (μg/kg) | Control (μg/kg) | PETROX ® 1 (μg/kg) | Control (μg/kg) | PETROX ® 1 (μg/kg) | Control (μg/kg) |
| Benzo(a)anthracene | ND | ND | 70.6 | 66.1 | NA | NA |
| Benzo(a)pyrene | 140 | 110 | ND | 95.9 | 100 | 13 |
| Benzo(b)fluoranthene | 210 | 197 | 172 | 174 | 18 | 12 |
| Benzo(g,h,i)perylene | ND | 107 | ND | 83.2 | NA | 23 |
| Benzo(k)fluoranthene | ND | ND | ND | 78.7 | NA | 11 |
| Chrysene | 231 | 207 | 156 | 154 | 33 | 26 |
| Fluoranthene | 264 | 203 | 160 | 127 | 40 | 38 |
| Pyrene | 344 | 343 | 196 | 201 | 43 | 41 |

Results from treating samples contaminated with gasoline, diesel, and oils for 21 days with PETROX® 1 are shown in Table III.

TABLE III

RESULT USING 21 DAY PETROX ® 1 TREATMENT

Contaminant

| | | | | | | |
|---|---|---|---|---|---|---|
| Gasoline Range Hydrocarbons | 5.6 | ND | ND | 6.97 | 100 | NA |
| Diesel & Heavy Oil Range Hydrocarbons | 1220 | 1070 | 894 | 772 | 27 | 28 |

ND = not detected;
NA = not applicable

With respect to benzo(b)fluoranthene, the PETROX®-treated materials were bioremediated faster than the control samples. After three weeks of PETROX® treatment, the concentration of benzo(b)fluoranthene was reduced from 210 μg/kg to 172 μg/kg (18% reduction). In contrast, the concentration of benzo(b)fluoranthene was reduced from 197 μg/kg to 174 μg/kg (13% reduction). After three weeks of PETROX® treatment, the concentration of chrysene was reduced from 231 μg/kg to 156 μg/kg (33% reduction). In contrast, the concentration of chrysene in the control samples was reduced from 207 μg/kg to 154 μg/kg (26% reduction). After three weeks of PETROX®-treatment, the concentration of each of fluoranthene and pyrene, the concentration of fluoranthene was reduced from 264 μg/kg to 160 μg/kg (40% reduction), and the concentration of pyrene was reduced from 344 μg/kg to 196 μg/kg (43% reduction). The concentration of fluoranthene in the control samples was reduced from 203 μg/kg to 127 μg/kg (38% reduction), and the concentration of pyrene was reduced from 343 μg/kg to 201 μg/kg (41%). The PETROX®-treated samples had a similar rate of degradation as the control samples with respect to the degradation of diesel and heavy oil range hydrocarbons. For example, the PETROX®-treated samples had 27% reduction in diesel and heavy oil range hydrocarbons, from 1220 mg/kg to 894 mg/kg, while the control samples had 28% reduction in diesel and heavy oil range hydrocarbons, from 1070 mg/kg to 772 mg/kg.

Example 2

Following the method described in Example 1, street debris containing a relatively high concentration of organic nutrients is bioremediated. Debris from many areas of the country contains relatively large amounts of vegetation, particularly during the late summer and fall. Such debris includes leaves, grasses, foliage, branches, soil, compost, plant matter, etc.

The street sweeping debris to be remediated is formed in a windrow and is controlled for temperature by adjusting moisture content and windrow dimensions. Because vegetation itself provides a microbial consortium with an abundant nutrient supply, bioremediation occurs faster than with debris containing less vegetation, and the increased rate naturally increases the windrow's internal temperature. To maintain the bioremediation activity of heat-sensitive microorganisms, the windrow internal temperature is regulated by increasing its moisture content and/or decreasing its volume.

The above-described streep sweeping debris is formed into a windrow about one foot height (i.e., half the height as in Example 1) with about the same length and width as in Example 1. The windrow is aerated with a SCAT windrow turner. The material is contacted with the microbial consortium solution during aeration as previously described in Example 1, wherein the microbial population within the windrow is from about $1 \times 10^6$ cfu/ml to about $1 \times 10^9$ cfu/ml. The test area is equipped with a water sprinkling system such that the windrow is periodically watered to maintain a moisture content of about 10% to about 30% and a temperature of about 95° F. Because the vegetation provides a nutrient source for added microorganisms, as described in Example 1, no additional nutrients are supplied.

Bioremediation occurs under these conditions for about 21 days, with monitoring to ensure desired moisture, pH, oxygen levels, etc. are maintained within the windrow. After 21 days, the contaminant levels in the windrow are reduced.

Example 3

Following the methods described in Example 1, street sweeping debris containing a relatively high concentration of sand is bioremediated. Such debris occurs year round in coastal and desert regions of the U.S., and during the winter in regions of the U.S. where sand is applied to roads during and preparatory to snow accumulation. Typically, street sweeping debris containing large amounts of sand does not contain large amounts of vegetation, and street sweeping debris containing large amounts of vegetation does not contain large amounts of sand.

Where the street sweeping debris contains a relatively high concentration of sand, and thus a relatively low concentration of vegetation, temperature control of the windrow becomes less important. Because this debris contains few if any nutrients for the microbial consortium, applied as in Example 1, its bioremediation rate is slower. Decreased bioremediation activity decreases the need to control the windrow's internal temperature by maintaining relatively high moisture content. Thus, the windrow dimensions are increased relative to those of Example 2.

This street sweeping debris is formed into a windrow about three feet high (about twice the height as in Example 1), with about the same length and width as in Example 1. The windrow is aerated with a SCAT windrow turner. The material is contacted with the microbial consortium solution during aeration as previously described, wherein the microbial population within the windrow is from about $1 \times 10^6$ cfu/ml to about $1 \times 10^9$ cfu/ml. The test area is equipped with a water sprinkling system such that the windrow is periodically watered in order to maintain a moisture content of about 10% to about 15% and a temperature of about 95° F. The windrow is supplemented with microbial nutrients to obtain and maintain a desired bioremediation rate Bioremediation occurs under these conditions for about 21 days with monitoring to ensure desired moisture, pH, oxygen levels, etc. are maintained within the windrow. After 21 days, the contaminant levels in the windrow are reduced.

Example 4

Any type of street sweeping debris is contacted with a microbial consortium before it is collected in a hopper of the sweeper. Many metropolitan areas use mechanical broom sweepers in their street sweeping operations. Mechanical broom sweepers typically comprise at least two circular brooms on the bottom of the vehicle wherein the circular brooms contact the street surface and gather the debris. The debris is then swept onto a conveyor and collected in a hopper.

To control dust created from mechanical broom sweepers, many metropolitan areas pretreat the street surface with water. Some areas dispense water from a vehicle separate from the mechanical broom sweeper vehicle to pretreat the street surface, in which case the water-pretreatment vehicle proceeds the sweeper vehicle and sprays the street surface with water contained in a tank. The tank may contain over 1000 gal of water.

In one embodiment, a lyophilized bioremediation composition, resulting in a viable freeze dried form, is contained in a drum liner package. Four liners, each containing lyophilized PETROX® are fit into each of four 55 gallon drums, and 55 gallons of water is added to each drum to rehydrate the microorganisms. The drums are maintained from about 75° F. to about 95° F. for about 24 hours, after which the solution in each drum is transferred into the tank of the water-pretreatment vehicle. Additional water is added to the tank to result in about 500 gallons of the microbial solution. It will be appreciated by one skilled in the art that larger or smaller volumes of microbial solution may be prepared to utilize different tank capacities. Using the water-dispensing solutions (e.g., sprays, hoses, jets, pulses, etc.), the microbial solution is applied to the street surface to contact the contaminated material before it is gathered into the sweeper hopper, that is, bioremediation is initiated during water pretreatment of the street for dust control. The mechanical broom sweeper, following behind the water dispensing vehicle, collects the contaminated material already in contact with the microbial consortium, that is, already undergoing bioremediation.

In another embodiment, a mechanical broom sweeper equipped with a sweeper spray nozzle is used to pretreat a street surface with water. The above-described microbial solution is transferred to the tank of a mechanical broom sweeper equipped with a sweeper spray nozzle, with other processes occurring as previously described.

Depending upon the extent and type of contaminants, hopper dimensions, hopper mixing capability, ambient conditions, distance to the collection site, etc., the material may be at least partially bioremediated before it reaches a collection site. Alternatively, the material may be substantially bioremediated before it reaches a collection site. The extent of bioremediation is relative, such that even partial bioremediation decreases contaminant levels such that any toxicity is reduced. In one embodiment, toxicity may be sufficiently reduced to render the debris meeting requirements for transport of non-toxic material.

At a collection site, at least partially bioremediated material is formed into a windrow of appropriate volume. The windrow is aerated with a SCAT windrow turner. The test area is equipped with a water sprinkling system such that the windrow is periodically watered in order to maintain moisture content of about 10% to about 30% and a temperature up to about 95° F. The contaminated material is bioremediated for a period of about 21 days while maintaining desired pH and oxygen levels. After 21 days, the contaminant levels in the windrow are reduced.

Example 5

The microbial consortium is contacted with the street sweeping debris as the debris is collected in a hopper of a street sweeping vehicle. Contact may occur by fitting a mechanical broom sweeper with a spray nozzle connected to a holding tank, where the spray nozzle is positioned above the conveyor and/or in the hopper.

In this embodiment, the microbial solution is prepared as previously described and transferred to a holding tank. If the mechanical broom sweeper is fit with the spray nozzle above the conveyor, the microbial consortium is sprayed onto the contaminated material as the contaminated material is collected onto the conveyor. If the mechanical broom sweeper is fit with the spray nozzle in the sweeper hopper, the microbial consortium is contacted with the contaminated material as the material is collected within the sweeper hopper. It will be appreciated by one skilled in the art that the hoppers of regenerative air sweepers, sometimes referred to as vacuum sweepers, and dry-vacuum sweepers may be fit with a spray nozzle such that the contaminated material is contacted with the microbial consortium in the sweeper hopper.

The contaminated material, in contact with the microbial solution, is transported to a treatment site and formed into a windrow having a desired volume. The windrow is aerated with a SCAT windrow turner. The test area is equipped with a water sprinkling system such that the windrow is periodically watered in order to maintain a moisture content of about 10% to about 30% and a temperature of up to about 95° F. The street debris is bioremediated for a period of about 21 days while maintaining desired pH and oxygen levels within the windrow. After 21 days, the contaminant levels in the windrow are reduced.

Other variations or embodiments of the composition and method will also be apparent to one of ordinary skill in the art from the above description and examples. Thus, the forgoing embodiments are not to be construed as limiting the scope of the following claims.

What is claimed is:

1. A bioremediation method for street cleaning, comprising providing a composition consisting essentially of at least one genus of *Pseudomonas* to street sweeping debris collected in a street cleaning process, the composition provided under conditions sufficient to reduce a level of at least one contaminant in the debris, resulting in at least partially bioremediated debris, the composition selected from the group consisting of
    (a) a combination of *Pseudomonas putida* strains B and E,
    (b) a combination of *Pseudomonas fluorencens* strain F and *Pseudomonas putida* strain I,
    (c) a combination of *Pseudomonas putida* strains B and E and *Pseudomonas fluorencens* strain G,
    (d) *Pseudomonas putida* strain B,
    (e) *Pseudomonas putida* strain E,
    (f) *Pseudomonas putida* strain I,
    (g) *Pseudomonas fluorencens* strain F, and combinations thereof.

2. The method of claim 1 wherein the composition in (a) is a 50:50 mixture of *Pseudomonas putida* strain B and *Pseudomonas putida* stain E.

3. The method of claim 1 wherein the composition in (a) is a combination of *Pseudomonas putida* strains B and E, present in an amount ratio ranging from 5:95 to 95:5.

4. The method of claim 1 wherein the composition in (a) is a combination of *Pseudomonas putida* strains B and E, present in an amount ratio ranging from 20:80 to 80:20.

5. The method of claim 1 wherein the composition in (b) is a 50:50 mixture of *Pseudomonas fluorencens* strain F and *Pseudomonas putida* strain I.

6. The method of claim 1 wherein the composition in (b) is a combination of *Pseudomonas putida* strain I and *Pseudomonas fluorencens* strain F, present in an amount ratio ranging from 5:95 to 95:5.

7. The method of claim 1 wherein the composition in (b) is a combination of *Pseudomonas putida* strain I and *Pseudomonas fluorencens* strain F, present in an amount ratio ranging from 20:80 to 80:20.

8. The method of claim 1 wherein the composition is applied after collection of debris, during collection of debris, and/or before collection of debris.

9. The method of claim 1 further comprising transporting the debris to a site under conditions for transport of non-toxic material.

10. The method of claim 1 wherein the composition is applied in a street sweeping vehicle.

11. The method of claim 1 wherein the composition is applied to the debris with mixing.

12. The method of claim 1 wherein the conditions include at least one of regulated moisture, oxygen, temperature, or pH.

13. The method of claim 1 wherein the bioremediated debris is maintained at about 10% moisture to about 30% moisture.

14. The method of claim 1 wherein the bioremediated debris is maintained at a concentration selected from the group consisting of
- about 1 mg oxygen per 1 L water to about 15 mg oxygen per 1 L water,
- about 3 mg oxygen per 1 L water to about 12 mg oxygen per 1 L water,
- about 5 mg oxygen per 1 L water to about 10 mg oxygen per 1 L water,
- about 15% by volume to about 25% by volume,
- about 17% by volume to about 24% by volume,
- about 19% by volume to about 21% by volume, and
- about 21% by volume.

15. The method of claim 1 wherein the bioremediated debris is maintained at a temperature ranging from about 75° F. to about 95° F.

16. The method of claim 1 wherein the bioremediated debris is subjected to the composition up to about 21 days.

17. A bioremediation method for street cleaning comprising
applying a composition, the composition consisting essentially of at least one *Pseudomonas* genus in a concentration ranging from about $1\times10^6$ cfu/ml to about $1\times10^9$ cfu/ml and at least one nutrient, to street cleaning debris collected from a metropolitan street cleaning process to be bioremediated resulting in a treated material, the composition applied under conditions sufficient to reduce a level of at least one contaminant in the treated material, the conditions selected from the group consisting of maintenance of about 10% to about 30% moisture, about 15% oxygen to about 21% oxygen, about 75° F. to about 95° F. temperature, and combinations thereof, for a time sufficient to result in a bioremediated material, wherein the at least one *Pseudomonas* genus is selected from the group consisting of
  (a) a combination of *Pseudomonas putida* strains B and E,
  (b) a combination of *Pseudomonas fluorencens* strain F and *Pseudomonas putida* strain I,
  (c) a combination of *Pseudomonas putida* strains B and E and *Pseudomonas fluorencens* strain G,
  (d) *Pseudomonas putida* strain B,
  (e) *Pseudomonas putida* strain E,
  (f) *Pseudomonas putida* strain I, and
  (g) *Pseudomonas fluorencens* strain F.

18. The method of claim 17 resulting in a reduction in the treated material of at least one of a petroleum contaminant.

19. The method of claim 17 wherein the time is up to 21 days.

20. A bioremediation method for street cleaning comprising
providing a composition consisting essentially of a combination of *Pseudomonas putida* strain B and *Pseudomonas putida* strain E, and optionally *Pseudomonas fluorencens* strain G, to street sweeping debris collected in a street cleaning process to result in a treated material, and
determining bioremediation of the treated material by measuring degradation of petroleum contaminants in the treated material.

* * * * *